(12) United States Patent
Guillon et al.

(10) Patent No.: US 8,629,073 B2
(45) Date of Patent: *Jan. 14, 2014

(54) CATALYST COMPRISING AN IZM-2 ZEOLITE AND AT LEAST ONE METAL, AND ITS USE IN THE TRANSFORMATION OF HYDROCARBONS

(75) Inventors: Emmanuelle Guillon, Vourles (FR); Nicolas Cadran, Oullins (FR); Sylvie Maury, Charly (FR); Amandine Cabiac, Lyons (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 289 days.

This patent is subject to a terminal disclaimer.

(21) Appl. No.: 13/057,812

(22) PCT Filed: Jul. 21, 2009

(86) PCT No.: PCT/FR2009/000899
§ 371 (c)(1),
(2), (4) Date: Apr. 6, 2011

(87) PCT Pub. No.: WO2010/015733
PCT Pub. Date: Feb. 11, 2010

(65) Prior Publication Data
US 2011/0190562 A1    Aug. 4, 2011

(30) Foreign Application Priority Data
Aug. 8, 2008 (FR) ..................... 08 04559

(51) Int. Cl.
*B01J 29/06* (2006.01)
*C07C 1/20* (2006.01)
*C07C 1/24* (2006.01)
*C07C 2/12* (2006.01)
*C07C 5/22* (2006.01)
*C07C 5/00* (2006.01)

(52) U.S. Cl.
USPC .................. 502/60; 502/63; 502/64; 502/66; 502/73; 502/74; 585/324; 585/326; 585/329; 585/330; 585/477; 585/481; 585/639; 585/640; 585/733; 585/734; 585/739

(58) Field of Classification Search
USPC .............. 502/60, 63, 64, 66, 73, 74; 585/400, 585/477, 324, 326, 329, 330, 481, 639, 640, 585/733, 734, 739
See application file for complete search history.

(56) References Cited

U.S. PATENT DOCUMENTS

| 4,539,193 | A | 9/1985 | Valyocsik |
| 5,207,893 | A | 5/1993 | Iwamoto et al. |
| 7,771,703 | B2 * | 8/2010 | Guillon et al. ............. 423/703 |
| 2006/0210472 | A1 | 9/2006 | Hastoy et al. |
| 2009/0326288 | A1 * | 12/2009 | Mamadov et al. .......... 585/259 |
| 2010/0272624 | A1 * | 10/2010 | Fecant et al. ............. 423/327.1 |
| 2011/0180455 | A1 * | 7/2011 | Bouchy et al. ................ 208/49 |
| 2011/0192765 | A1 * | 8/2011 | Guillon et al. ............. 208/110 |
| 2012/0022279 | A1 * | 1/2012 | Cabiac et al. ............... 554/167 |

FOREIGN PATENT DOCUMENTS

| EP | 1 702 888 A1 | 9/2006 |
| EP | 1 953 118 A1 | 8/2008 |
| WO | WO 2009/004131 A1 | 1/2009 |
| WO | WO 2009/144411 A2 | 12/2009 |
| WO | WO 2009/144412 A2 | 12/2009 |

OTHER PUBLICATIONS

International Search Report of PCT/FR2009/000899 (Jan. 6, 2010).

* cited by examiner

*Primary Examiner* — Elizabeth Wood
(74) *Attorney, Agent, or Firm* — Millen, White, Zelano & Branigan, P.C.

(57) ABSTRACT

A catalyst is described which comprises at least one IZM-2 zeolite, at least one matrix and at least one metal selected from metals from groups VIII, VIB and VIIB, said zeolite having a chemical composition expressed as the anhydrous base in terms of moles of oxides by the following general formula: $XO_2:aY_2O_3:bM_{2/n}O$, in which X represents at least one tetravalent element, Y represents at least one trivalent element and M is at least one alkali metal and/or alkaline-earth metal with valency n, a and b respectively representing the number of moles of $Y_2O_3$ and $M_{2/n}O$; and a is in the range 0.001 to 0.5 and b is in the range 0 to 1.

20 Claims, No Drawings

CATALYST COMPRISING AN IZM-2 ZEOLITE AND AT LEAST ONE METAL, AND ITS USE IN THE TRANSFORMATION OF HYDROCARBONS

The present invention relates to the field of zeolitic catalysts and to their use in various processes for the transformation of hydrocarbon feeds. More precisely, the present invention relates to a catalyst comprising at least one IZM-2 zeolite, at least one matrix and at least one metal selected from metals from groups VIII, VIIB and VIIB.

PRIOR ART

Microporous crystalline materials such as zeolites or silicoaluminophosphates are solids which are widely used in the oil industry as catalysts, catalyst supports, adsorbants or separation agents. Although many microporous crystalline structures have been discovered, the refining and petrochemicals industry is constantly seeking out novel zeolitic structures which have particular properties for applications such as purification or separation of gases, or the conversion of carbonaceous or other species. The properties of a zeolitic catalyst are greatly dependent on the porous structure of the zeolite it contains, on its stability and on its acidity.

SUMMARY AND ADVANTAGE OF THE INVENTION

The present invention concerns a catalyst comprising at least one IZM-2 zeolite and at least one matrix and at least one metal selected from metals from groups VIII, VIIB and VIIB of the periodic classification of the elements, said zeolite having an X ray diffraction diagram including at least one of the peaks recorded in Table 1 and having a chemical composition expressed as the anhydrous base in terms of moles of oxides by the following general formula: $XO_2:aY_2O_3:bM_{2/n}O$, in which X represents at least one tetravalent element, Y represents at least one trivalent element and M is at least one alkali metal and/or alkaline-earth metal with valency n, a and b respectively representing the number of moles of $Y_2O_3$ and $M_{2/n}O$; and a is in the range 0.001 to 0.5 and b is in the range 0 to 1.

Said catalyst in accordance with the invention is advantageously used to carry out various processes for the transformation of hydrocarbon feeds. In particular, said catalyst of the invention produces interesting catalytic performances when it is used in the isomerization of aromatic compounds containing 8 carbon atoms, in the transalkylation of alkylaromatic compounds, in the hydroisomerization of light linear paraffins and in the transformation of alcohols.

DETAILED DESCRIPTION OF THE INVENTION

The present invention concerns a catalyst comprising at least one IZM-2 zeolite, at least one matrix and at least one metal selected from metals from groups VIII, VIIB and VIIB of the periodic classification of the elements, said zeolite having an X ray diffraction diagram including at least the peaks recorded in Table 1 below:

TABLE 1

Mean values of $d_{hkl}$ and relative intensities measured on an X ray diffraction diagram of the calcined IZM-2 zeolite

| 2 theta (°) | $d_{hkl}$ (Å) | $I_{rel}$ |
|---|---|---|
| 5.07 | 17.43 | Vw |
| 7.36 | 12.01 | Vs |
| 7.67 | 11.52 | Vs |
| 8.78 | 10.07 | S |
| 10.02 | 8.82 | Vw |
| 12.13 | 7.29 | Vw |
| 14.76 | 6.00 | Vw |
| 15.31 | 5.78 | Vw |
| 15.62 | 5.67 | Vw |
| 16.03 | 5.52 | Vw |
| 17.60 | 5.03 | Vw |
| 18.22 | 4.87 | Vw |
| 19.01 | 4.66 | Vw |
| 19.52 | 4.54 | Vw |
| 21.29 | 4.17 | M |
| 22.44 | 3.96 | W |
| 23.10 | 3.85 | Mw |
| 23.57 | 3.77 | W |
| 24.65 | 3.61 | Vw |
| 26.78 | 3.33 | W |
| 29.33 | 3.04 | Vw |
| 33.06 | 2.71 | Vw |
| 36.82 | 2.44 | Vw |
| 44.54 | 2.03 | Vw | in which: Vs=very strong; S=strong; M=medium; Mw=medium weak; W=weak; Vw=very weak, and having a chemical composition expressed as the anhydrous base in terms of moles of oxides by the following general formula: $XO_2:aY_2O_3:bM_{2/n}O$, in which X represents at least one tetravalent element, Y represents at least one trivalent element and M is at least one alkali metal and/or alkaline-earth metal with valency n, a and b respectively representing the number of moles of $Y_2O_3$ and $M_{2/n}O$; and a is in the range 0.001 to 0.5, b is in the range 0 to 1.

The diffraction diagram the data for which is given in Table 1 is obtained by radiocrystallographic analysis using a diffractometer employing the conventional powder technique with the $K_{\alpha1}$ peak of copper ($\lambda=1.5406$ Å). Starting from the position of the diffraction peaks represented by the angle 2θ, the characteristic interplanar spacings $d_{hkl}$ of the sample are calculated using the Bragg relationship. The error in the measurement $\Delta(d_{hkl})$ of $d_{hkl}$ is calculated by the Bragg relationship as a function of the absolute error $\Delta(2\theta)$ in the measurement of 2θ. An absolute error $\Delta(2\theta)$ of ±0.02° is customarily acceptable. The relative intensity $I_{rel}$ in each value of $d_{hkl}$ is measured from the height of the corresponding diffraction peak. The X ray diffraction diagram of the IZM-2 zeolite present in the catalyst of the invention comprises at least the peaks at the values of $d_{hkl}$ given in Table 1. In the $d_{hkl}$ column, the mean values of the interplanar spacings are shown in Angstroms (Å). Each of these values must be supplemented with an error measurement $\Delta(d_{hkl})$ in the range ±0.6 Å to ±0.01 Å.

The IZM-2 zeolite present in the catalyst of the invention has a chemical composition expressed as the anhydrous base in terms of moles of oxides defined by the following general formula: $XO_2:aY_2O_3:bM_{2/n}O$, in which X represents at least one tetravalent element, Y represents at least one trivalent element and M is at least one alkali metal and/or alkaline-earth metal with valency n. In said formula given hereinabove, a represents the number of moles of $Y_2O_3$ and a is in the range 0.001 to 0.5, preferably in the range 0.001 to 0.05, more preferably in the range 0.001 to 0.02; b represents the number of moles of $M_{2/n}O$ and is in the range 0 to 1, preferably in the range 0 to 0.5, more preferably in the range 0.005 to 0.5.

In accordance with the invention, X is preferably selected from silicon, germanium, titanium and a mixture of at least two of these tetravalent elements; more preferably, X is silicon and Y is preferably selected from aluminium, boron, iron, indium and gallium; more preferably, Y is aluminium. In the IZM-2 zeolite present in the catalyst of the invention, X is preferably silicon and Y is preferably aluminium. M is preferably selected from lithium, sodium, potassium, rubidium, caesium, calcium, magnesium and barium and a mixture of at least two of said metals; highly preferably, M is sodium and/or caesium.

The IZM-2 zeolite present in the catalyst of the invention and containing X and Y atoms as defined above, preferably aluminium atoms and silicon atoms, has an overall X/Y atomic ratio, preferably an overall Si/Al atomic ratio, in the range 5 to 100, preferably in the range 10 to 50 and more preferably in the range 10 to 35. The zeolite present in the catalyst of the invention may also be dealuminated. Highly advantageously, the IZM-2 zeolite present in the catalyst of the invention is in the protonated form (hydrogen form, $H^+$), in which the proportion of cations other than $H^+$ is less than 30% of the total number of cations, preferably less than 20% and more preferably less than 5% with respect to the total number of cations on the zeolite. In accordance with the invention, when the IZM-2 zeolite is in the protonated form, coefficient b is zero in the formula: $XO_2:aY_2O_3:bM_{2/n}O$ given above.

In accordance with the invention, said catalyst comprises at least one metal selected from metal from groups VIIB, VIIB and VIII of the periodic classification of the elements. Said catalyst comprises either a metal selected from metal from groups VIIB, VIIB and VIII or several metals as a mixture selected from metals from groups VIIB, VIIB and VIII. Chromium and molybdenum are preferred metals from group VIB. Rhenium is a preferred metal from group VIIB. Nickel, ruthenium, rhodium, palladium, osmium, iridium and platinum are preferred metals from group VIII; highly preferably, said metal from group VIII is selected from palladium, nickel and platinum.

The matrix present in the catalyst of the invention is a porous mineral matrix, generally amorphous. It is selected from elements from the group formed by aluminas, silicas, magnesia, amorphous silica-aluminas, natural clays (kaolin, bentonite, sepiolite, attapulgite), titanium oxide, boron oxide, zirconia, phosphates of aluminium, phosphates of titanium, phosphates of zirconium, charcoal and mixtures thereof. Preferably, a matrix containing alumina is used, particularly in all of its forms known to the skilled person, more preferably gamma alumina. Further, mixtures of alumina and silica, mixtures of alumina and silica-alumina may advantageously be used.

Said catalyst of the invention advantageously comprises at least one additional metal selected from metals from groups IIIA and IVA of the periodic classification of the elements, preferably selected from gallium, indium, tin and mixtures thereof, highly preferably selected from indium, tin and mixtures thereof. In particular, the catalyst of the invention advantageously comprises at least one metal from group VIII of the periodic classification of the elements, preferably platinum or palladium, and at least one metal selected from metals from groups IIIA and IVA, preferably indium and tin.

The catalyst of the invention is free of any sulphide phase.
More particularly, said catalyst of the invention contains:

1% to 90%, preferably 3% to 80% and more preferably 4% to 60% by weight of said IZM-2 zeolite;

0.01% to 4%, preferably 0.05% to 2% by weight of at least one metal selected from metals from groups VIIB, VIIB and VIII of the periodic classification of the elements;

optionally, 0.01% to 2%, preferably 0.05% to 1% by weight of at least one additional metal selected from metals from groups IIIA and IVA of the periodic classification of the elements;

at least one matrix providing the complement to 100% of the catalyst.

Said catalyst of the invention is preferably in the form of beads or extrudates, preferably in the form of extrudates. It has mechanical properties such that the value for the bed crush strength, determined using the Shell method (SMS 1471-74), is preferably more than 0.7 MPa.

The present invention also pertains to the preparation of the catalyst of the invention. Preparation of the catalyst of the invention commences with preparation of the IZM-2 zeolite.

Said IZM-2 zeolite present in the catalyst of the invention is prepared using a process in which the following are reacted: an aqueous mixture comprising at least one source of at least one oxide $XO_2$, at least one source of at least one oxide $Y_2O_3$, at least one source of at least one alkali and/or alkaline-earth metal, and at least one organic species R comprising two quaternary nitrogen atoms, the mixture preferably having the following molar composition:

| | |
|---|---|
| $XO_2/Y_2O_3$ | at least 2, preferably at least 20, more preferably 55 to 600; |
| $H_2O/XO_2$ | 1 to 100, preferably 10 to 70; |
| $R/XO_2$ | 0.02 to 2, preferably 0.05 to 0.5; |
| $M_{2/n}O/XO_2$ | 0.001 to 1, preferably 0.005 to 0.5; | where X is one or more tetravalent element(s) selected from the group formed by the following elements: silicon, germanium and titanium, preferably silicon, where Y is one or more trivalent element(s) selected from the group formed by the following elements: aluminium, iron, boron, indium and gallium, preferably aluminium, and where M is one or more alkali and/or alkaline-earth metal(s) selected from lithium, sodium, potassium, rubidium, caesium, calcium, magnesium, barium and a mixture of at least two of these metals, preferably sodium.

R is an organic species having two quaternary nitrogen atoms acting as an organic template. Preferably, R is the nitrogen-containing compound 1,6-bis(methylpiperidinium) hexane, which has the following developed formula:

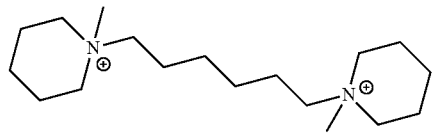 [SMILES: C[N+]1(CCCCCC[N+]2(C)CCCCC2)CCCCC1]

The anions associated with the quaternary ammonium cations present in the organic species template for synthesis of the IZM-2 zeolite present in the catalyst of the invention are selected from the acetate anion, the sulphate anion, the carboxylate anion, the tetrafluoroborate anion, halide anions such as the fluoride, the chloride, the bromide, the iodide, the hydroxide anion and a combination of several of these. Preferably, the anions associated with the quaternary ammonium cations present in the template species for synthesis of the IZM-2 zeolite are selected from the hydroxide anion and the bromide anion. Said organic nitrogen-containing species used as the template for the IZM-2 zeolite is synthesized using any method which is known to the skilled person. In order to synthesize 1,6-bis(methylpiperidinium)hexane dibromide, one mole of 1,6-dibromohexane is mixed with at least 2 moles of N-methylpiperidine in ethanol. Generally, the mixture is heated under reflux for a period in the range 3 to 10 hours. After filtration, then precipitation using an etherified solvent such as diethylether then re-crystallization from an ethanol/ether mixture, the 1,6-bis(methylpiperidinium)hexane dibromide is obtained. 1,6-bis(methylpiperidinium)hexane dihydroxide is preferably obtained by treatment, at ambient temperature, of an aqueous solution of the 1,6-bis (methylpiperidinium)hexane dibromide using silver oxide, $Ag_2O$.

The source of the element X employed to carry out the process for preparing the IZM-2 zeolite may be any compound comprising the element X and which can liberate that element in aqueous solution in the reactive form. Advantageously, when the element X is silicon, the silica source may be any one of those currently used in synthesizing zeolites, for example solid powdered silica, silicic acid, colloidal silica, dissolved silica or tetraethoxysilane (TEOS). Examples of powdered silicas which may be used are precipitated silicas, in particular those obtained by precipitation from a solution of an alkali metal silicate, such as aerosil silicas, pyrogenic silicas, for example "CAB-O-SIL", and silica gels. It is possible to use colloidal silicas having different particle sizes, for example with a mean equivalent diameter in the range 10 to 15 nm or between 40 and 50 nm, such as those sold under trade names such as "LUDOX". Preferably, the silicon source is LUDOX-HS-40.

The source of element Y which may optionally be used to carry out the process for the preparation of the IZM-2 zeolite may be any compound comprising the element Y which can liberate that element in aqueous solution in the reactive form. In the preferred case in which Y is aluminium, the source of alumina is preferably sodium aluminate, or an aluminium salt, for example the chloride, nitrate, hydroxide or sulphate, an aluminium alkoxide or alumina proper, preferably in the hydrated or hydratable form, such as colloidal alumina, pseudoboehmite, gamma alumina or alpha or beta trihydrate. It is also possible to use mixtures of the sources cited above.

The source of the alkali and/or alkaline-earth metal M is advantageously a halide or a hydroxide of said metal M, preferably a hydroxide of said metal M.

In order to carry out the process for preparing the IZM-2 zeolite, it is preferable that the aqueous mixture comprising at least one source of at least one oxide $XO_2$, at least one source of at least one oxide $Y_2O_3$, at least one source of at least one alkali and/or alkaline-earth metal, and at least one organic species R containing two quaternary nitrogen atoms, also comprises at least one source of hydroxide ions. Said source of hydroxide ions advantageously derives from the organic template species R when it is in the hydroxide form, namely 1,6-bis(methylpiperidinium)hexane dihydroxide, or a source of alkali metal and/or alkaline-earth metal M when it is in the hydroxide form, for example sodium hydroxide.

Additionally, in accordance with a preferred implementation of the process for preparing the IZM-2 zeolite present in the catalyst of the invention, an aqueous mixture comprising an oxide of silicon, alumina, 1,6-bis(methylpiperidinium) hexane dibromide and sodium hydroxide is reacted.

The process for preparing the IZM-2 zeolite present in the catalyst of the invention consists of preparing an aqueous reaction mixture known as a gel and comprising at least one source of at least one oxide $XO_2$, at least one source of at least one oxide $Y_2O_3$, at least one organic species R, and at least one source of at least one alkali and/or alkaline-earth metal. The quantities of said reagents are adjusted so as to provide said gel with a composition allowing it to crystallize into IZM-2 zeolite in the as-synthesized form with general formula (I): $XO_2:aY_2O_3:bM_{2/n}O; cR; dH_2O$, where a, b and n satisfy the criteria defined above, c represents the number of moles of R and is in the range 0.005 to 2, preferably in the range 0.01 to 0.5, and d represents the number of moles of $H_2O$ and is in the range 0.005 to 2, preferably in the range 0.01 to 1. Next, the gel undergoes a hydrothermal treatment until the IZM-2 zeolite forms. The gel is advantageously subjected to hydrothermal conditions under autogenous reaction pressure, optionally by adding gas, for example nitrogen, at a temperature in the range 120° C. to 200° C., preferably in the range 140° C. to 180° C., and more preferably in the range 160° C. to 175° C. until solid IZM-2 zeolite crystals are formed in its as-synthesized form. The time necessary to obtain crystallization generally varies between 1 hour and several months depending on the composition of the reagents in the gel, the stirring and the reaction temperature. Preferably, the crystallization period is in the range 2 hours to 21 days. The reaction is generally carried out with stifling or in the absence of stifling, preferably in the presence of stirring.

It may be advantageous to add seeds to the reaction mixture to reduce the time necessary for the formation of crystals and/or to reduce the total crystallization period. It may also be advantageous to use seeds to encourage the formation of the IZM-2 zeolite to the detriment of the impurities. Such seeds comprise solid crystals, especially crystals of IZM-2 zeolite. The crystalline seeds are generally added in a proportion in the range 0.01% to 10% by weight of oxide $XO_2$ used in the reaction mixture.

At the end of the hydrothermal treatment step resulting in crystallization of the IZM-2 zeolite, the solid phase is filtered and washed to obtain the IZM-2 zeolite in its as-synthesized form which is then dried and calcined to obtain the zeolite in the calcined form. The calcining step is advantageously implemented by means of one or more heating steps carried out at a temperature in the range 100° C. to 1000° C., preferably in the range 400° C. to 650° C., for a period in the range from a few hours to several days, preferably in the range 3 hours to 48 hours. Preferably, calcining is carried out in two consecutive heating steps. At the end of said calcining step, the IZM-2 zeolite obtained is that with an X ray diffraction diagram including at least the peaks set out in Table 1. It is free of water and of the organic species R present in the IZM-2 zeolite in the as-synthesized form.

The invention also concerns the preparation of said catalyst. In order to prepare the catalyst of the invention, in general, said IZM-2 zeolite, either in its as-synthesized form or in its calcined form, initially undergoes at least one ion exchange step, for example using at least one solution of $NH_4NO_3$, in order to eliminate at least a portion, preferably practically all of the alkali cation, in particular sodium, present in the cationic position in the zeolite and to thereby obtain said IZM-2 zeolite in the hydrogen form. When said ion exchange step(s) is (are) carried out on an as-synthesized IZM-2 zeolite, the zeolite obtained thereby in its hydrogen form generally undergoes a step for calcining in a stream of dry air, which is intended to eliminate the organic template occluded in the micropores of the zeolite.

At this stage, the zeolite may undergo any type of treatment known to the skilled person aimed at stabilizing, dealuminating or passivating it.

Preparation of the Catalyst is Continued by Mixing the Matrix and the Prepared Zeolite then forming it. The catalyst of the invention is generally formed so that the catalyst is preferably in the form of extrudates or beads, for use thereof. The conditions for forming the zeolite, the choice of matrix, any prior milling of the zeolite, the peptization process, the addition of pore-forming agents, the mixing time, the extrusion pressure if the catalyst is in the form of extrudates, and the drying speed and time are determined for each matrix as a function of rules which are well known to the skilled person, in order to obtain a catalyst that is preferably in the form of extrudates or beads.

Preparation of the Catalyst is Generally Continued by Calcining, Normally at a temperature in the range 250° C. to 600° C., preferably preceded by drying, for example oven drying, at a temperature which is generally in the range from ambient temperature to 250° C., preferably in the range 40° C. to 200° C. Said drying step is preferably carried out during the temperature ramp-up necessary to carry out said calcining.

The IZM-2 zeolite may be formed from the as-synthesized zeolite, i.e. containing the organic template and the alkali cations, generally sodium. In this case the step for calcining in a stream of dry air, which is aimed at eliminating the organic template, and the ion exchange steps using at least one solution of $NH_4NO_3$, are carried out on the formed catalyst comprising the zeolite and the matrix. However, and highly preferably, the ion exchange step(s), for example using at least one solution of $NH_4NO_3$, carried out to obtain said IZM-2 zeolite present in the catalyst of the invention in the hydrogen form, is (are) carried out before forming.

Deposition of at least one metal selected from metals from groups VIII, VIIB and VIIB of the periodic classification of the elements and optionally of at least one additional metal selected from metals from groups IIIA and IVA of the periodic classification of the elements may be carried out at any time during the preparation, either before forming or during mixing of the zeolite and the matrix, the zeolite being mixed with the ensemble constituted by the precursor(s) of said metal(s) and the matrix or, as is preferable, after forming.

When the addition of at least one metal selected from metals from groups VIIB, VIIB and VIII and optionally at least one additional metal selected from metals from groups IIIA and IVA is carried out after forming, said metal(s) may then be added either before calcining or, as is preferable, after calcining of the matrix-zeolite mixture. Said added metal(s) is(are) generally deposited either practically completely on the zeolite or partially on the zeolite and partially on the matrix or, as is preferable, practically completely on the matrix, this being carried out, in a manner which is known to the skilled person, by appropriate choice of the parameters used during said deposition, such as the nature of the precursor of said metal(s), for example. Deposition of at least one metal selected from metals from groups VIIB, VIIB and VIII is generally carried out using the techniques of dry impregnation, excess impregnation or, as is preferable, by ion exchange(s). In the case of ion exchange from precursors based on platinum and/or palladium, platinum and/or palladium salts are routinely used such as hexachloroplatinic acid and/or hexachloropalladic acid, in the presence or absence of competing agent(s) such as hydrochloric acid, for example. In the case in which at least one additional metal selected from metals from groups IIIA and IVA of the periodic classification of the elements is also introduced, any of the deposition techniques known to the skilled person and any precursors are suitable for introducing said additional metal.

In the case in which the catalyst contains several metals selected from metals from groups VIIB, VIIB and VIII of the periodic classification of the elements, the metals may be introduced either all in the same manner or using different techniques, and in any order. In the case in which at least one metal selected from metals from groups IIIA and IVA of the periodic classification of the elements is also introduced, the metals selected from the metals from groups VIIB, VIIB and VIII and those selected from metals from groups IIIA or IVA may be added either separately or simultaneously in at least one unitary step. When at least one metal selected from metals from groups IIIA and IVA is added separately, it is preferable that it should be added prior to the metal(s) selected from metals from groups VIIB, VIIB and VIII. In the case in which the deposition technique employed is that of ion exchange, several successive exchanges may be necessary in order to introduce the required quantities of metals.

The metal(s) selected from metals from groups VIIB, VIIB and VIII is(are) advantageously deposited in the matrix in the acid form of ammoniacal compounds or compounds such as nitrates and chlorides, for example. For platinum, hexachloroplatinic acid or platinum tetramine salts are preferably selected. For Re, perrhenic acid is preferred. For Ni, Ni nitrate is preferred. For Mo, ammonium heptamolybdate is preferred.

Preferably, when the catalyst of the invention comprises at least one noble metal, for example platinum or palladium, ammoniacal compounds are advantageously employed as a precursor. In this case, the noble metal will be deposited on the zeolite.

In the case of platinum, it is possible, for example, to cite platinum II tetramine salts with formula $Pt(NH_3)_4X_2$, platinum IV hexamine salts with formula $Pt(NH_3)_6X_4$; platinum IV halogenopentamine salts with formula $(PtX(NH_3)_5)X_3$; platinum N-tetrahalogenodiamine salts with formula $PtX_4(NH_3)_2$; complexes of platinum with halogen-polyketones and halogenated compounds with formula $H(Pt(acac)_2X)$; X being a halogen selected from the group formed by chlorine, fluorine, bromine and iodine, with X preferably being chlorine, and acac representing the group $C_5H_7O_2$ derived from acetylacetone.

The introduction of at least one noble metal from the platinum family is preferably carried out by impregnation using an aqueous or organic solution of one of the organometallic compounds mentioned above. Of the organic solvents which may be used, it is possible to cite paraffinic, naphthenic or aromatic hydrocarbons, and organic halogenated compounds containing 1 to 12 carbon atoms per molecule, for example. Examples which may be cited are n-heptane, methylcyclohexane, toluene and chloroform. Mixtures of solvents may also be used.

The additional metal, optionally introduced in addition, selected from metals from groups IIIA and IVA, may be introduced via compounds such as, for example, chlorides, bromides or nitrates, alkyls of metals from groups IIIA and IVA, i.e., for example for tin and indium, alkyl tins, or indium nitrate and chloride.

If the additional metal is introduced before the noble metal, the compound of said additional metal used is generally selected from the group constituted by the halide, nitrate, acetate, tartrate, carbonate and oxalate of the metal. Introduction is thus advantageously carried out in aqueous solution. However, it may also be introduced using a solution of an organometallic compound of the metal, for example tetrabutyltin in the case of tin. In this case, before proceeding to the introduction of at least one noble metal, calcining in air is carried out.

Said additional metal may also be introduced in the form of at least one organic compound selected form the group constituted by complexes of said metal, in particular polyketone complexes of the metal and hydrocarbyl metals such as metal alkyls, cycloalkyls, aryls, alkylaryls and arylalkyls. In this latter case, the metal is advantageously introduced using a solution of an organometallic compound of said metal in an organic solvent. It is also possible to use organohalogenated compounds of a metal. Particular examples of additional metal compounds that may be cited are tetrabutyltin in the case of tin, and triphenylindium in the case of indium.

The impregnation solvent is selected from the group constituted by paraffinic, naphthenic or aromatic hydrocarbons containing 6 to 12 carbon atoms per molecule and organic halogenated compounds containing 1 to 12 carbon atoms per molecule. Examples which may be cited are n-heptane, methylcyclohexane and chloroform. It is also possible to use mixtures of the solvents defined above.

Deposition of at least one metal selected from metals from groups VIIB, VIIB and VIII and optionally at least one metal selected from metals from groups IIIA and IVA is preferably followed by calcining in air or oxygen, generally in the range 250° C. to 600° C., preferably in the range 350° C. to 550° C., for a period in the range 0.5 to 10 hour(s), preferably in the range 1 to 4 hour(s). Next, an optional reduction in hydrogen may be carried out, generally at a temperature in the range 300° C. to 600° C., preferably in the range 350° C. to 550° C., for a period in the range 1 to 10 hour(s), preferably in the range 2 to 5 hours, in order to obtain said metal(s) principally in the reduced form necessary for catalytic activity.

As an example, one of the preferred methods for the preparation of the catalyst of the invention consists of initially causing said IZM-2 zeolite, either in the as-synthesized form or in its calcined form, to undergo at least one ion exchange step, for example with at least one solution of $NH_4NO_3$, in order to obtain said zeolite in its hydrogen form. Said IZM-2 zeolite exchanged thereby is then mixed in a moist gel of matrix (generally obtained by mixing at least one acid and a matrix powder), for example alumina, for a period necessary to obtain good homogeneity of the paste obtained thereby, i.e. for about ten minutes, for example, then passing said paste through a die to form extrudates, for example with a diameter in the range 0.4 to 4 mm, preferably in the range 0.4 to 2.5 mm and more preferably in the range 0.8 to 2.0 mm. Next, after drying and calcining, the metal(s) selected from metals from groups VIIB, VIIB and VIII, for example platinum, and optional metal(s) selected from metals from groups IIIA and IVA is(are) deposited, for example by ion exchange, using, for example, hexachloroplatinic acid, in the presence of a competing agent (for example hydrochloric acid), said deposition being followed by calcining, for example for approximately 2 hours at approximately 400° C.

Irrespective of the implementation for the preparation of the catalyst of the invention, the catalyst of the invention may be pre-reduced ex situ in a stream of hydrogen, for example at a temperature of 450° C. to 600° C., for a period of 0.5 to 4 hours.

In the case in which the catalyst contains no sulphur, the metal is reduced in hydrogen in situ before injecting the feed.

In the case in which the catalyst of the invention contains sulphur, the sulphur is introduced into the formed, calcined catalyst containing the metal or metals cited above, either in situ before the catalytic reaction, or ex situ. Any sulphurization is carried out before reduction. In the case of in situ sulphurization, if the catalyst has not been pre-reduced, then reduction is carried out before sulphurization. In the case of ex situ sulphurization, reduction then sulphurization is carried out. Sulphurization is carried out in the presence of hydrogen using any sulphurizing agent which is well known to the skilled person, such as dimethyl sulphide or hydrogen sulphide. As an example, the catalyst is treated with a feed containing dimethyl sulphide in the presence of hydrogen, in a concentration such that the sulphur/metal atomic ratio is 1.5. The catalyst is then kept for approximately 3 hours at approximately 400° C. in a stream of hydrogen before injecting the feed.

The present invention also pertains to processes for the transformation of hydrocarbons in the presence of at least said catalyst of the invention. The hydrocarbon transformations of the invention primarily concern isomerization of aromatic compounds containing 8 carbon atoms, transalkylation of alkylaromatic compounds, hydroisomerization of light linear paraffins and transformation of alcohols.

More precisely, in a further aspect, the present invention provides a process for the isomerization of a cut containing at least one aromatic compound containing eight carbon atoms per molecule, said process comprising bringing said aromatic cut into contact with at least said catalyst of the invention present in at least one catalytic reactor. In particular, said aromatic cut containing at least one aromatic compound containing eight carbon atoms per molecule comprises, as the aromatic compound containing eight carbon atoms per molecule, either solely a mixture of xylenes, or solely ethylbenzene, or a mixture of xylene(s) and ethylbenzene. Said isomerization process is generally carried out under the following operating conditions:

a temperature of 300° C. to 500° C., preferably 320° C. to 450° C. and more preferably 340° C. to 430° C.;
a partial pressure of hydrogen of 0.3 to 1.5 MPa, preferably 0.4 to 1.2 MPa and more preferably 0.7 to 1.2 MPa;
a total pressure of 0.45 to 1.9 MPa, preferably 0.6 to 1.5 MPa; and
a space velocity, expressed in kilograms of feed introduced per kilogram of catalyst per hour, of 0.25 to 30 $h^{-1}$, preferably 1 to 10 $h^{-1}$ and more preferably 2 to 6 $h^{-1}$.

Preferably, the catalyst used to carry out said isomerization process of the invention comprises at least one IZM-2 zeolite, at least one matrix and at least one metal from group VIII, preferably platinum or palladium. Highly advantageously, it also comprises at least one additional metal selected from metals from groups IIIA and IVA. It may also comprise a quantity of sulphur such that the ratio of the number of sulphur atoms to the number of atoms of metal(s) from group VIII is in the range 0.5:1 to 2:1.

The present invention also provides a process for the transalkylation of alkylaromatic hydrocarbons to produce xylenes, said process comprising bringing said alkylaromatic hydrocarbons into contact with at least said catalyst of the invention present in at least one catalytic reactor. Preferably, the transalkylation process of the invention is a process for the transalkylation of toluene and alkylaromatic hydrocarbons containing at least 9 carbon atoms per molecule ($AC_9^+$), preferably trimethylbenzenes, to produce xylenes. The feed used to carry out said transalkylation process of the invention is generally formed from a toluene-$AC_9^+$ mixture which may contain 0.1% to 100% by weight of $AC_9^+$ with respect to the total mixture. Said catalyst of the invention has proved to be highly effective for said use, as it has proved to be particularly active, selective and stable, even in the presence of feeds to be treated containing a large quantity of heavy $AC_9^+$ aromatics, said heavy aromatics possibly containing a high proportion of $AC_{10}^+$. Thus, $AC_9^+$ feeds containing at least 5% and up to 25% by weight, and even more of $AC_{10}^+$, can be upgraded. Non-exhaustive examples which may be cited are dimethylethylbenzenes, diethylbenzenes and propylethylbenzenes. The use of said catalyst of the invention in the transalkylation of heavy alkylaromatics is thus of particular advantage.

The operating conditions for carrying out the process for the transalkylation of alkylaromatic hydrocarbons of the invention are generally as follows: a temperature in the range 250° C. to 650° C., preferably in the range 350° C. to 550° C.; a pressure in the range 1 to 6 MPa and preferably in the range 2 to 4.5 MPa; a space velocity, expressed in kilograms of feed introduced per kilogram of catalyst per hour, in the range 0.1 to 10 $h^{-1}$, preferably in the range 0.5 to 4 $h^{-1}$; and a molar ratio of hydrogen to hydrocarbons in the range 2 to 20, preferably in the range 3 to 12 mol/mol.

Preferably, the catalyst used for the transalkylation of alkylaromatic hydrocarbons comprises at least one IZM-2 zeolite, at least one alumina matrix and at least one metal from group VIIB, preferably rhenium.

The present invention also provides a process for hydroisomerization of paraffins present in a feed comprising, as a major portion, linear paraffins containing 5 to 8 carbon atoms per molecule, said process comprising bringing said feed into contact with at least said catalyst of the invention. Preferably, the sum of the quantities of linear paraffins containing 7 or 8 carbon atoms per molecule contained in the feed is in the range 2% to 90% by weight, preferably in the range 5% to 90% by weight, more preferably in the range 20% to 90% by weight, and highly preferably in the range 40% to 90% by weight with respect to the feed. Said feed is treated in at least one reaction zone containing at least said catalyst of the invention, preferably disposed in a fixed bed.

The operating conditions for carrying out said hydroisomerization process in accordance with the invention are generally as follows:
   a temperature of 30° C. to 300° C., preferably 70° C. to 300° C. and more preferably 80° C. to 280° C.;
   a total pressure of 0.10 to 18 MPa, preferably 0.5 to 10 MPa; more preferably 2 to 5 MPa;
   an hourly space velocity (HSV), defined as the mass of feed to be treated per mass of catalyst per hour, in the range 0.2 to 10 $h^{-1}$, preferably in the range 0.3 to 5 $h^{-1}$ and more preferably in the range 0.5 to 2 $h^{-1}$;
   a $H_2$/HC molar ratio in the range 0.05 to 20, preferably in the range 0.2 to 10.

Preferably, the catalyst used for the hydroisomerization of paraffins comprises at least one IZM-2 zeolite, at least one alumina matrix and at least one metal from group VIII, preferably platinum or palladium.

In a further aspect, the invention pertains to a process for the transformation of at least one aliphatic compound containing 1 to 18 carbon atoms and carrying an alcohol function, said process being carried out in the presence of at least one catalyst of the invention.

Preferably, said aliphatic compound carrying an alcohol function comprises 1 to 12 carbon atoms, more preferably 1 to 6 carbon atoms. Still more preferably, said aliphatic compound carrying an alcohol function is selected from ethanol and pentanol. Said aliphatic compound containing 1 to 18 carbon atoms and carrying an alcohol function may be linear or branched. Preferably, it is a monoalcohol. The use of completely anhydrous alcohols is not necessary for carrying out said process for the transformation of at least one aliphatic compound containing 1 to 18 carbon atoms and carrying an alcohol function.

In accordance with a first implementation of said process for the transformation of at least one aliphatic compound containing 1 to 18 carbon atoms and carrying an alcohol function, said transformation which is employed is a dehydration reaction during which said aliphatic compound carrying an alcohol function is dehydrated to olefin(s) with the production of water. In accordance with said first mode, ethanol is preferably used as an aliphatic compound having an alcohol function in order to produce ethylene. The operating conditions for carrying out said process for the transformation of alcohols to olefins are as follows: the total pressure is less than 2 MPa, preferably in the range 0.05 to 1 MPa, the temperature is in the range 150° C. to 400° C., preferably in the range 200° C. to 300° C. The HSV, defined as the mass flow rate at which the feed comprising said aliphatic compound is introduced divided by the mass of catalyst, thus depends on the alcohol present in said feed and generally is in the range 0.5 to 50 $h^{-1}$, preferably in the range 1 to 25 $h^{-1}$. An inert gas such as nitrogen, for example, or a light hydrocarbon may be used to dilute the feed comprising said aliphatic compound at the level of the catalyst.

Said process for the transformation of alcohols to olefins in accordance with said first implementation is advantageously carried out in a fixed, moving or fluidized bed. Apart from the water generated during the dehydration reaction, the ethers associated with the alcohols introduced into the reactor are principally formed in the case of methanol and ethanol. Said ethers may advantageously be recycled in order to increase the yield of olefins.

In accordance with a second implementation of said process for the transformation of at least one aliphatic compound containing 1 to 18 carbon atoms and carrying an alcohol function, said transformation which is employed simultaneously carries out, in the same reactor, dehydration of said aliphatic compound into olefin(s) and oligomerization of said olefin(s). It produces hydrocarbons which will be incorporated into the gasoline pool and/or into the diesel pool. The operating conditions for carrying out such a transformation are such that the temperature is in the range 250° C. to 450° C., the total pressure is in the range 2 to 10 MPa and the HSV, corresponding to the mass flow rate at which the feed comprising said aliphatic compound is introduced divided by the mass of catalyst, is in the range 0.1 to 5 $h^{-1}$. The increase in pressure for carrying out said second implementation over said first implementation (dehydration) favours the formation of compounds derived from the oligomerization of olefins formed in situ in the reactor(s). The catalyst based on IZM-2 of the invention is preferentially activated, preferably by subjecting it to calcining, prior to bringing it into contact in the reactor with the feed comprising said aliphatic compound under the reaction conditions cited above. An inert gas such as nitrogen or a light hydrocarbon is advantageously used to dilute the feed at the level of the catalyst.

A variation of said second implementation of the transformation process of the invention consists of separating the implementation of the dehydration step from that of oligomerization of the olefins formed in the dehydration step. In accordance with said variation, a separator is advantageously installed between the reactor used for the dehydration of alcohols to olefins and the reactor used for the transformation of olefins into heavier compounds. The dehydration reaction and the oligomerization reaction may be carried out in the presence of a catalyst based on a IZM-2 zeolite of the invention, or the dehydration reaction may be carried out in the presence of a catalyst comprising a zeolite which is different from IZM-2 zeolite, a silica-alumina or an activated alumina, and the oligomerization reaction may be carried out in the presence of a catalyst based on a IZM-2 zeolite of the invention.

Irrespective of the implementation employed for the transformation of a feed comprising at least one aliphatic compound carrying an alcohol function, the reaction for the transformation of said feed by dehydration or by dehydration then oligomerization may be carried out in any type of reactor known to the skilled person. In accordance with a first implementation, said process for the transformation of said feed is carried out in at least one fixed bed reactor. The catalyst is then preferably located in a radial bed reactor in order to minimize the pressure drop through the catalytic bed. In accordance with a second implementation, said process for the transformation of said feed is carried out in at least one moving bed reactor. One or more reactors with one or more moving beds may be used, possibly with staggered injection of the feed, and coupled or not coupled with a continuous regeneration system.

In accordance with said process for the transformation of a feed comprising at least one aliphatic compound carrying an alcohol function in accordance with the invention, the reaction effluent is kept at its reaction pressure, not counting any pressure drops in the equipment employed. The effluent is cooled to below the dew point of water. In said second implementation (dehydration+oligomerization), said cooled reaction effluent is introduced into a device which can carry out three-phase separation of a gas phase constituted by light olefins in particular, an organic liquid (gasoline and gas oil) and an aqueous liquid (water, untransformed alcohol, dissolved hydrocarbons).

The following examples illustrate the invention without limiting its scope.

EXAMPLES

Example 1

Preparation of 1,6-bis(methylpiperidinium)hexane Dibromide for the Preparation of IZM-2 Zeolites (Z1 and Z2)

50 g of 1,6-dibromohexane (0.20 mole, 99%, Alfa Aesar) was added to a 1 L flask containing 50 g of N-methylpiperidine (0.51 mole, 99%, Alfa Aesar) and 200 mL of ethanol. The reaction medium was stirred and heated under reflux for 5 h. The mixture was then cooled to ambient temperature and filtered. The mixture was poured into 300 mL of cold diethylether, then the precipitate formed was filtered and washed with 100 mL of diethylether. The solid obtained was re-crystallized from an ethanol/ether mixture. The solid obtained was vacuum dried for 12 h. 71 grams of a white solid was obtained (i.e. a yield of 80%). The product had the expected $^1$H NMR spectrum. $^1$H NMR ($D_2O$, ppm/TMS): 1.27 (4H, m); 1.48 (4H, m); 1.61 (4H, m); 1.70 (8H, m); 2.85 (6H, s); 3.16 (12H, m).

Example 2

Preparation of an IZM-2 Zeolite in its Hydrogen Form 20.134 g of a colloidal suspension of silica, known under the trade name Ludox HS-40 sold by Aldrich, was incorporated into a solution composed of 0.253 g of sodium aluminate (Carlo Erba), 1.555 g of sodium hydroxide (Prolabo), 9.888 g of 1,6-bis(methylpiperidinium)hexane dibromide and 68.170 g of deionized water. The molar composition of the mixture was as follows: $SiO_2$; 0.01 $Al_2O_3$; 0.17 $Na_2O$; 0.17 1,6-bis(methylpiperidinium)hexane; 33.33 $H_2O$. The mixture was stirred vigorously for half an hour. Following homogenization, the mixture was transferred into an autoclave. The autoclave was heated for 9 days at 170° C. with stifling (250 rpm). The crystalline product obtained was filtered, washed with deionized water (to obtain a neutral pH) then dried overnight at 100° C. The solid was introduced into a muffle furnace where calcining was carried out: the calcining cycle comprised a temperature ramp-up to 200° C., a stage at 200° C. for 2 hours, a temperature ramp-up to 550° C. followed by a stage at 550° C. for 8 hours, then a return to ambient temperature.

The calcined solid was analyzed by X ray diffraction and identified as being constituted by IZM-2 zeolite.

Said IZM-2 zeolite was then brought into contact for 2 hours at ambient temperature with an aqueous solution of 1 mole of ammonium chloride using 50 mL of solution per gram of solid calcined product. The zeolite was then filtered, washed with deionized water and dried at 110° C. This treatment was repeated 3 times. The zeolite was then calcined in air for 24 hours, at 550° C. It was in its hydrogen form.

Example 3

Preparation of Catalyst C1 Comprising a IZM-2 Zeolite, Chromium and an Alumina Matrix (in Accordance with the Invention)

The IZM-2 zeolite in its hydrogen form, prepared in accordance with Example 2, underwent a step for dry impregnation with an aqueous chromium sulphate solution. The product was then dried at 110° C. for 18 hours and calcined in air for 12 hours at 550° C. The quantity by weight of chromium in the product constituted by IZM-2 zeolite in the hydrogen form and chromium was 0.21%. Said product was mixed with a type SB3 alumina gel from the supplier Sasol. The mixed paste was then extruded through a 1.4 mm diameter die. The extrudates obtained thereby were calcined at 500° C. for 2 hours in air. The catalyst C1 thus obtained was constituted by 40% by weight of alumina, 59.87% by weight of IZM-2 zeolite and 0.13% by weight of $Cr_2O_7$. Said IZM-2 zeolite had a chemical composition with the formula $SiO_2$: 0.0125 $Al_2O_3$ (a=0.0125), i.e. a Si/Al ratio equal to 40.

Example 4

Preparation of Catalyst C2 Comprising a IZM-2 Zeolite (H Form), Nickel and an Alumina Matrix (in Accordance with the Invention)

The IZM-2 zeolite in its hydrogen form, prepared in accordance with Example 2, underwent a step for dry impregnation with an aqueous nickel sulphate solution. The product was then dried at 110° C. for 18 hours and calcined in air for 12 hours at 550° C. The quantity by weight of nickel in the product constituted by IZM-2 zeolite in the hydrogen form and nickel was 0.23%. Said product was mixed with a type SB3 alumina gel from the supplier Sasol. The mixed paste was then extruded through a 1.4 mm diameter die. The extrudates obtained thereby were calcined at 500° C. for 2 hours in air. Catalyst C2 was thus obtained constituted by 40% by weight of alumina, 59.86% by weight of IZM-2 zeolite and 0.14% by weight of NiO. Said IZM-2 zeolite had a chemical composition with the formula $SiO_2$:0.0125 $Al_2O_3$ (a=0.0125), i.e. a Si/Al ratio equal to 40.

Example 5

Transformation of Alcohols Under Pressure (in Accordance with the Invention)

In this example, the performances of catalysts C1 and C2 in the transformation of ethanol under pressure during two different tests were evaluated in succession.

For each of the tests, a fixed traversed bed pilot unit was loaded with 1.5 g of catalyst C1, C2 respectively. Before carrying out each of the tests, catalysts C1 and C2 were activated at 550° C. in air for 2 h.

To carry out each of the tests, the ethanol was diluted with nitrogen so that the $N_2$/ethanol molar ratio was equal to 4. At the outlet from the reactor, the gas phase was separated from the organic liquid phase and from the aqueous liquid phase. In addition to the experimental conditions, Table 2 indicates the mass balance for the organic products recovered. These are divided into three categories: gases, liquids with low boiling points (bp<150° C.) and liquids with high boiling points (bp>150° C.).

TABLE 2

Operating conditions and performances of catalysts C1 and C2 in the transformation of ethanol under pressure

| | Catalyst | |
|---|---|---|
| | C1 | C2 |
| Conditions | | |
| T (° C.) | 300 | 300 |
| P (MPa) | 3 | 3 |
| HSV ($h^{-1}$) | 1.2 | 1.2 |
| *TOS (h) | 5 | 5 |
| Ethanol conversion (%) | 100% | 100.0% |
| Distribution of products in outlet effluent (% by weight) | | |
| Gas | 22.1% | 20.2% |
| Liquid (bp <150° C.) | 38.5% | 35.8% |
| Liquid (bp >150° C.) | 39.4% | 44% |

*TOS (time on stream) represents the contact time of the catalyst with the feed.

The conversion and yield were calculated as follows:

Conversion=(mass flow rate of alcohol$_{inlet}$−mass flow rate of alcohol$_{outlet}$)/mass flow rate of alcohol$_{inlet}$.

The results shown in Table 2 demonstrate that the catalysts C1 and C2 of the invention are highly active in the transformation of alcohols under pressure and result in products that can readily be incorporated into the gasoline pool (liquid phase having a boiling point of less than 150° C.) and into the diesel pool (liquid phase having a boiling point of more than 150° C.).

Example 6

Preparation of Catalyst C3 Comprising a IZM-2 Zeolite (H Form), Platinum and an Alumina Matrix (in Accordance with the Invention)

20.138 g of a colloidal suspension of silica, known under the trade name Ludox HS-40 sold by Aldrich, was incorporated into a solution composed of 0.211 g of sodium aluminate (Carlo Erba), 1.577 g of sodium hydroxide (Prolabo), 9.890 g of 1,6-bis(methylpiperidinium)hexane dibromide and 68.252 g of deionized water. The molar composition of the mixture was as follows: $SiO_2$; 0.008 $Al_2O_3$; 0.17 $Na_2O$; 0.17 1,6-bis(methylpiperidinium)hexane; 33.33 $H_2O$. The mixture was stirred vigorously for half an hour. Following homogenization, the mixture was transferred into an autoclave. The autoclave was heated for 9 days at 170° C. with stifling (250 rpm). The crystalline product obtained was filtered, washed with deionized water (to obtain a neutral pH) then dried overnight at 100° C. The as-synthesized solid obtained was analyzed by X ray diffraction and identified as being constituted by IZM-2 zeolite.

Said IZM-2 zeolite in its as-synthesized form underwent four ion exchanges in a 10N $NH_4NO_3$ solution at approximately 100° C. over 4 hours for each exchange in order to obtain said IZM-2 zeolite in the hydrogen form. It was then formed by extrusion with an alumina gel. The extrudates obtained underwent dry calcining at 550° C. in a stream of dry air for 10 hours in order to eliminate the organic template. 1% by weight of platinum was deposited on said extrudates by dry impregnation using $Pt(NH_3)_4Cl_2$. After placing in an oven (110° C., 12 h) and calcining in air (2 L/h/g) at 420° C., catalyst C3 was obtained, constituted by 89.10% by weight of alumina, 9.90% by weight of IZM-2 zeolite and 1% by weight of platinum. Said IZM-2 zeolite had a chemical composition with formula $SiO_2$: 0.0094 $Al_2O_3$ (a=0.0094), i.e. a Si/Al ratio equal to 53.

Example 7

Evaluation of Catalytic Properties of Catalyst C3 in the Isomerization of Aromatic Compounds Containing 8 Carbon Atoms (in Accordance with the Invention)

The performances of catalyst C3 were evaluated in the isomerization of an aromatic feed solely containing ethylbenzene.

The operating conditions for isomerization were as follows:

temperature: 410° C.;

total pressure: 1 MPa;

partial pressure of hydrogen: 0.8 MPa;

hourly space velocity, expressed as kilograms of feed introduced per kilogram of catalyst per hour, equal to 8.7 $h^{-1}$.

The catalyst was introduced into the reaction zone where it was initially reduced in hydrogen for 4 hours at 480° C., then the feed was introduced into said reaction zone where it was brought into contact with said catalyst C3.

The catalyst was evaluated in terms of ethylbenzene conversion and xylene selectivity. The results are shown in Table 3.

The xylenes yield was determined from the % by weight of xylenes produced, calculated from the data obtained from chromatographic analysis of each effluent.

The ethylbenzene conversion is the percentage by weight of ethylbenzene consumed.

The xylenes selectivity was calculated by means of the yield of xylenes produced. The selectivity was equal to the ratio of the yield of xylenes over the ethylbenzene conversion.

TABLE 3

Performances of catalyst C3 in the isomerization of aromatic compounds containing 8 carbon atoms after 4000 min of reaction

| | Catalyst C3 |
|---|---|
| Ethylbenzene conversion (%) | 33.5 |
| Xylenes selectivity (%) | 62.1 |
| Xylenes yield (%) | 20.8 |

Example 8

Preparation of Catalyst C4 Comprising a IZM-2 Zeolite (H Form), Rhenium and an Alumina Matrix (in Accordance with the Invention)

An as-synthesized IZM-2 zeolite was prepared using the same protocol and the same operating conditions (quantity of reagents and operating conditions proper) as those given for the preparation of the as-synthesized IZM-2 zeolite prepared in Example 6.

Said IZM-2 zeolite in its as-synthesized form underwent four ion exchanges in a 10N $NH_4NO_3$ solution at approximately 100° C. over 4 hours for each exchange in order to obtain said IZM-2 zeolite in the hydrogen form. It was then formed by extrusion with an alumina gel. The extrudates obtained underwent dry calcining at 550° C. in a stream of dry air for 10 hours in order to eliminate the organic template. They were then impregnated with an aqueous solution of ammonium perrhenate in order to deposit 0.3% by weight of rhenium on the finished catalyst. The moist solid was then dried at 120° C. for 12 hours and calcined in a stream of dry air at a temperature of 500° C. for one hour. Catalyst C4 obtained thereby contained 79.7% by weight of IZM-2 zeolite, 20.0% of alumina and 0.3% of Re. Said IZM-2 zeolite had a chemical composition with formula $SiO_2$: 0.0094 $Al_2O_3$ (a=0.0094), i.e. a Si/Al ratio equal to 53.

Example 9

Catalytic Performances of Catalyst C4 in the Transalkylation of Aromatics (in Accordance with the Invention)

First of all, the catalyst C4 was reduced in hydrogen at 450° C. for 2 hours. Next, it was treated with a feed containing dimethyldisulphide (DMDS) at a concentration such that the sulphur/metal atomic ratio was 1.5. This treatment was carried out for 3 hours at 400° C., maintaining a hydrogen/hydrocarbon ratio of 4.

The catalytic test was carried out under the following operating conditions:
- temperature: 400° C.;
- total pressure: 3 MPa;
- $H_2$/HC: 5 mol/mol;
- HSV: 4 $h^{-1}$ (mass of feed per g of catalyst per hour).

Catalyst C4 was evaluated with a feed containing 50% by weight of toluene and 50% by weight of a feed A1 constituted by 32% by weight of ethyltoluene, 56% by weight of trimethylbenzene and 12% by weight of aromatics containing at least 10 carbon atoms. The results are shown in Table 4.

The overall conversion is the percentage by weight of feed consumed (50% by weight of toluene+50% by weight of $AC_9^+$ feed consumed).

The yield of reaction products was determined from the % by weight of products, calculated from the data obtained by chromatographic analysis of each effluent.

TABLE 4

Performances of catalyst C4 in the transalkylation of aromatic compounds

| | |
|---|---|
| Overall conversion (%) | 52.8 |
| Yields (wt %) | |
| Lights (C1-C4) | 10.1 |
| Benzene + xylenes | 42.8 |
| Ethylbenzene | 0.4 |
| Heavies | 1.9 |

Catalyst C4 of the invention was active in the process for the transalkylation of aromatic compounds containing at least 9 carbon atoms per molecule and resulted in a satisfactory (benzene+xylenes) yield.

Example 10

Preparation of Catalyst C5 Comprising a IZM-2 Zeolite (H Form), Platinum and an Alumina Matrix (in Accordance with the Invention)

20.144 g of a colloidal suspension of silica, known under the trade name Ludox HS-40 sold by Aldrich, was incorporated into a solution composed of 0.158 g of sodium aluminate (Carlo Erba), 1.604 g of sodium hydroxide (Prolabo), 9.893 g of 1,6-bis(methylpiperidinium)hexane dibromide and 68.200 g of deionized water. The molar composition of the mixture was as follows: $SiO_2$; 0.006 $Al_2O_3$; 0.17 $Na_2O$; 0.17 1,6-bis(methylpiperidinium)hexane; 33.33 $H_2O$. The mixture was stirred vigorously for half an hour. Following homogenization, the mixture was transferred into an autoclave. The autoclave was heated for 9 days at 170° C. with stifling (250 rpm). The crystalline product obtained was filtered, washed with deionized water (to obtain a neutral pH) then dried overnight at 100° C. The as-synthesized solid obtained was analyzed by X ray diffraction and identified as being constituted by IZM-2 zeolite.

Said IZM-2 zeolite in its as-synthesized form underwent four ion exchanges in a 10N $NH_4NO_3$ solution at approximately 100° C. over 4 hours for each exchange in order to obtain said IZM-2 zeolite in the hydrogen form. It was then formed by extrusion with an alumina gel. The extrudates obtained underwent dry calcining at 550° C. in a stream of dry air for 10 hours in order to eliminate the organic template. 1% by weight of platinum was deposited on said extrudates by dry impregnation using $Pt(NH_3)_4Cl_2$. After placing in an oven (110° C., 12 h) and calcining in air (2 L/h/g) at 420° C., catalyst C5 was obtained, constituted by 79.10% by weight of IZM-2 zeolite, 19.90% by weight of alumina and 1% by weight of platinum. Said IZM-2 zeolite had a chemical composition with formula $SiO_2$: 0.0067 $Al_2O_3$ (a=0.0067), i.e. a Si/Al ratio equal to 75.

Example 11

Catalytic Performances of Catalyst C5 in the Hydroisomerization of Paraffins (in Accordance with the Invention)

First of all, catalyst C5 was reduced in hydrogen in situ after loading into the reaction zone: after a constant temperature stage of one hour at 150° C., the catalyst was reduced at 450° C. for 1 hour in a stream of hydrogen (15 L/h/g).

The feed used to carry out the hydroisomerization test was composed of 25% by weight of nC5, 35% by weight of nC6 and 40% by weight of nC7. It was introduced into the reaction zone containing 150 g of reduced catalyst C5. The catalytic test was carried out under the following operating conditions:
- T=230° C.;
- Total P=3 MPa;

$H_2$/HC (molar)=1.5;
$H_2$ flow rate=4.5×10$^{-9}$ L/h;
HSV=1.01 h$^{-1}$ (mass of feed/mass of catalyst/h).

The results obtained are shown in Table 5. They are expressed as the conversion of the various constituents of the feed (the conversion corresponding to the percentage by weight of each of the constituents consumed) and the C5+ yield expressing the quantity by weight of C5+ products in the effluents, the complement to 100% corresponding to the C5− products derived from cracking of the constituents of the feed.

TABLE 5

Performances of catalyst C5 in paraffin hydroisomerization

| | |
|---|---|
| nC5 conversion | 15% |
| nC6 conversion | 37% |
| nC7 conversion | 56.6% |
| C5+ yield | 92.5% |

Catalyst C5 in accordance with the invention produced an optimal yield of C5+, which means that the discharging effluent contains products with a good octane number. The optimal value of the C5+ yield demonstrates that the cracking reactions are minimized (only 7.5% of products which cannot be upgraded were formed), favouring the selectivity for isomerized products, namely the target products of the reaction.

The invention claimed is:

1. A catalyst comprising at least one IZM-2 zeolite, at least one matrix and at least one metal selected from metals from groups VIII, VIB and VIM, said zeolite having an X ray diffraction diagram including at least the peaks recorded in the table below:

| 2 theta (°) | $d_{hkl}$ (Å) | $I_{rel}$ |
|---|---|---|
| 5.07 | 17.43 | Vw |
| 7.36 | 12.01 | Vs |
| 7.67 | 11.52 | Vs |
| 8.78 | 10.07 | S |
| 10.02 | 8.82 | Vw |
| 12.13 | 7.29 | Vw |
| 14.76 | 6.00 | Vw |
| 15.31 | 5.78 | Vw |
| 15.62 | 5.67 | Vw |
| 16.03 | 5.52 | Vw |
| 17.60 | 5.03 | Vw |
| 18.22 | 4.87 | Vw |
| 19.01 | 4.66 | Vw |
| 19.52 | 4.54 | Vw |
| 21.29 | 4.17 | M |
| 22.44 | 3.96 | W |
| 23.10 | 3.85 | Mw |
| 23.57 | 3.77 | W |
| 24.65 | 3.61 | Vw |
| 26.78 | 3.33 | W |
| 29.33 | 3.04 | Vw |
| 33.06 | 2.71 | Vw |
| 36.82 | 2.44 | Vw |
| 44.54 | 2.03 | Vw | in which: Vs=very strong; S=strong; M=medium; Mw=medium weak; W=weak; Vw=very weak, and having a chemical composition expressed as the anhydrous base in terms of moles of oxides by the following general formula: $XO_2$: $aY_2O_3$: $bM_{2/n}O$, in which X represents at least one tetravalent element, Y represents at least one trivalent element and M is at least one alkali metal and/or alkaline-earth metal with valency n, a and b respectively representing the number of moles of $Y_2O_3$ and $M_{2/n}O$; and a is in the range of 0.001 to 0.5, b is in the range of 0 to 1.

2. A catalyst according to claim 1, in which X is silicon and Y is aluminium.

3. A catalyst according to claim 1, in which said IZM-2 zeolite is in its protonated form in which the proportion of cations other than H$^+$ is less than 30% of the total number of cations on the zeolite.

4. A catalyst according to claim 1, comprising said metal from group VIB which is chromium or molybdenum.

5. A catalyst according to claim 1, comprising said metal from group VIIB which is rhenium.

6. A catalyst according to claim 1, comprising said metal from group VIII which is selected from palladium, nickel and platinum.

7. A catalyst according to claim 1, in which said matrix contains alumina.

8. A catalyst according to claim 1, comprising at least one additional metal selected from metals from groups IIA and IVA.

9. A catalyst according to claim 1, in the form of beads or extrudates.

10. A process for the isomerization of a cut containing at least one aromatic compound containing eight carbon atoms per molecule, said process comprising bringing said aromatic cut into contact with at least one catalyst in accordance with claim 1 in at least one catalytic reactor.

11. A process for the transalkylation of alkylaromatic hydrocarbons to produce xylenes, said process comprising bringing said alkylaromatic hydrocarbons into contact with at least one catalyst in accordance with claim 1 in at least one catalytic reactor.

12. A process for the hydroisomerization of paraffins present in a feed comprising, as a major portion, linear paraffins containing 5 to 8 carbon atoms per molecule, said process comprising bringing said feed into contact with at least one catalyst in accordance with claim 1.

13. A process for the transformation of at least one aliphatic compound containing 1 to 18 carbon atoms and carrying an alcohol function, said process being carried out in the presence of at least one catalyst in accordance with claim 1.

14. A process according to claim 13, in which said transformation is a dehydration reaction during which said aliphatic compound carrying an alcohol function is dehydrated into olefin(s) with the production of water.

15. A process according to claim 13, in which said transformation comprising, in the same reactor, dehydration of said aliphatic compound into olefin(s) and oligomerization of said olefin(s).

16. A catalyst according to claim 3, in which X is silicon and Y is aluminium.

17. A catalyst according to claim 4, in which X is silicon and Y is aluminium.

18. A catalyst according to claim 5, in which X is silicon and Y is aluminium.

19. A catalyst according to claim 6, in which X is silicon and Y is aluminium.

20. A catalyst according to claim 8, in which X is silicon and Y is aluminium.

* * * * *

UNITED STATES PATENT AND TRADEMARK OFFICE
CERTIFICATE OF CORRECTION

PATENT NO. : 8,629,073 B2  
APPLICATION NO. : 13/057812  
DATED : January 14, 2014  
INVENTOR(S) : Emmanuelle Guillon et al.

Page 1 of 1

It is certified that error appears in the above-identified patent and that said Letters Patent is hereby corrected as shown below:

In the Claims

Column 19, line 31, reads "VIM", should read --VIIB--;

Column 20, line 22, reads "IIA", should read --IIIA--.

Signed and Sealed this  
Third Day of June, 2014

Michelle K. Lee  
*Deputy Director of the United States Patent and Trademark Office*

UNITED STATES PATENT AND TRADEMARK OFFICE
CERTIFICATE OF CORRECTION

PATENT NO.        : 8,629,073 B2
APPLICATION NO. : 13/057812
DATED             : January 14, 2014
INVENTOR(S)       : Guillon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 348 days.

Signed and Sealed this
Twenty-second Day of September, 2015

Michelle K. Lee
*Director of the United States Patent and Trademark Office*